US012584198B2

(12) United States Patent
Gupta et al.

(10) Patent No.: US 12,584,198 B2
(45) Date of Patent: Mar. 24, 2026

(54) BIODEGRADABLE MAGNESIUM ALLOYS

(71) Applicant: National University of Singapore, Singapore (SG)

(72) Inventors: Manoj Gupta, Singapore (SG); Gururaj Parande, Singapore (SG); Vyasaraj Badarinath Manakari, Singapore (SG); Raymond Chung Wen Wong, Singapore (SG); Somasundaram Prasadh, Singapore (SG)

(73) Assignee: National University of Singapore, Singapore (SG)

( * ) Notice: Subject to any disclaimer, the term of this patent is extended or adjusted under 35 U.S.C. 154(b) by 915 days.

(21) Appl. No.: 17/756,753

(22) PCT Filed: Dec. 2, 2020

(86) PCT No.: PCT/SG2020/050711
§ 371 (c)(1),
(2) Date: Jun. 1, 2022

(87) PCT Pub. No.: WO2021/112764
PCT Pub. Date: Jun. 10, 2021

(65) Prior Publication Data
US 2023/0002866 A1      Jan. 5, 2023

(30) Foreign Application Priority Data
Dec. 2, 2019      (SG) ............................ 10201911501V

(51) Int. Cl.
*C22C 23/04*          (2006.01)
*A61L 27/04*          (2006.01)
(Continued)

(52) U.S. Cl.
CPC ............ *C22C 23/04* (2013.01); *A61L 27/047* (2013.01); *A61L 27/58* (2013.01); *A61L 31/022* (2013.01);
(Continued)

(58) Field of Classification Search
CPC .. B22F 3/115; B22F 9/08; B22F 9/082; C23C 4/12; C23C 4/123
See application file for complete search history.

(56) References Cited

U.S. PATENT DOCUMENTS

| | | | | |
|---|---|---|---|---|
| 2003/0068558 A1* | 4/2003 | Sato | ........................ | H01M 4/38 |
| | | | | 429/231.95 |
| 2016/0022863 A1 | 1/2016 | Decker et al. | | |

FOREIGN PATENT DOCUMENTS

| | | | | |
|---|---|---|---|---|
| CN | 101629260 A | 1/2010 | | |
| CN | 107824793 A | * 3/2018 | .............. | B22F 9/082 |

(Continued)

OTHER PUBLICATIONS

CN101629260A English language translation (Year: 2010).*

(Continued)

*Primary Examiner* — Sally A Merkling
*Assistant Examiner* — Sean P. O'Keefe
(74) *Attorney, Agent, or Firm* — Osha Bergman Watanabe & Burton LLP

(57) ABSTRACT

The present invention relates to a biodegradable alloy of Formula (I): Mg—Zn—X, wherein X represents —Ca—Mn or —Dy—Sr, wherein Zn is about 0.1 wt % to about 3.0 wt %, Dy is about 0.1 wt % to about 0.7 wt %, Sr is about 0.1 wt % to about 0.9 wt %, Ca is about 0.1 wt % to about 1.5 wt %, Mn is about 0.1 wt % to about 0.9 wt % and Mg is balance with impurities. The present invention further relates to a method for producing alloys, wherein the method comprises: (a) placing alloy components in a crucible, (Continued)

wherein the alloy components are placed in the crucible in a multilayer arrangement; (b) melting the alloy components at about 700° C. to about 850° C.; (c) stirring the melt of step (b) at about 400 rpm to about 500 rpm; (d) atomizing the melt of step (c) into millimeter size droplets using jets of inert gas; and (e) cooling and depositing the atomized alloy melt to obtain an ingot.

11 Claims, 10 Drawing Sheets

(51) Int. Cl.

| | |
|---|---|
| *A61L 27/58* | (2006.01) |
| *A61L 31/02* | (2006.01) |
| *A61L 31/14* | (2006.01) |
| *B22D 23/00* | (2006.01) |
| *C22C 1/02* | (2006.01) |
| *C22F 1/06* | (2006.01) |

(52) U.S. Cl.
CPC .............. *A61L 31/148* (2013.01); *C22C 1/02* (2013.01); *C22F 1/06* (2013.01); *B22D 23/003* (2013.01)

(56) References Cited

FOREIGN PATENT DOCUMENTS

| | | |
|---|---|---|
| CN | 109680195 A | 4/2019 |
| CN | 109972007 A | 7/2019 |

OTHER PUBLICATIONS

Gupta, M. et al., An Insight into Processing and Characteristics of Magnesium Based Composites,. 'Magnesium Technology, Dec. 31, 2014 (Year: 2014).*
Gupta, M. et al., Section 2. Synthesis of Magnesium Based Biomaterials. Insight into Designing Biocompatible Magnesium Alloys and Composites: Processing, Mechanical and Corrosion Characteristics, Jan. 14, 2015 (Year: 2015).*
International Search Report Issued in Application No. PCT/SG2020/050711, dated Mar. 5, 2021, 8 pages.
Written Opinion Issued in Application No. PCT/SG2020/050711, dated Mar. 5, 2021, 8 pages.
Parande, G. et al., "Enhancing Mechanical Response of Monolithic Magnesium Using Nano-NiTi (Nitinol) Particles," Metals, Dec. 2, 2018, vol. 8, No. 12, p. 1014: 1-13, 14 pages.
Gupta, M. et al., Section 2. Synthesis of Magnesium Based Biomaterials. Insight into Designing Biocompatible Magnesium Alloys and Composites: Processing, Mechanical and Corrosion Characteristics, Jan. 14, 2015, pp. 17-34, 18 pages.

* cited by examiner

[Fig. 1]
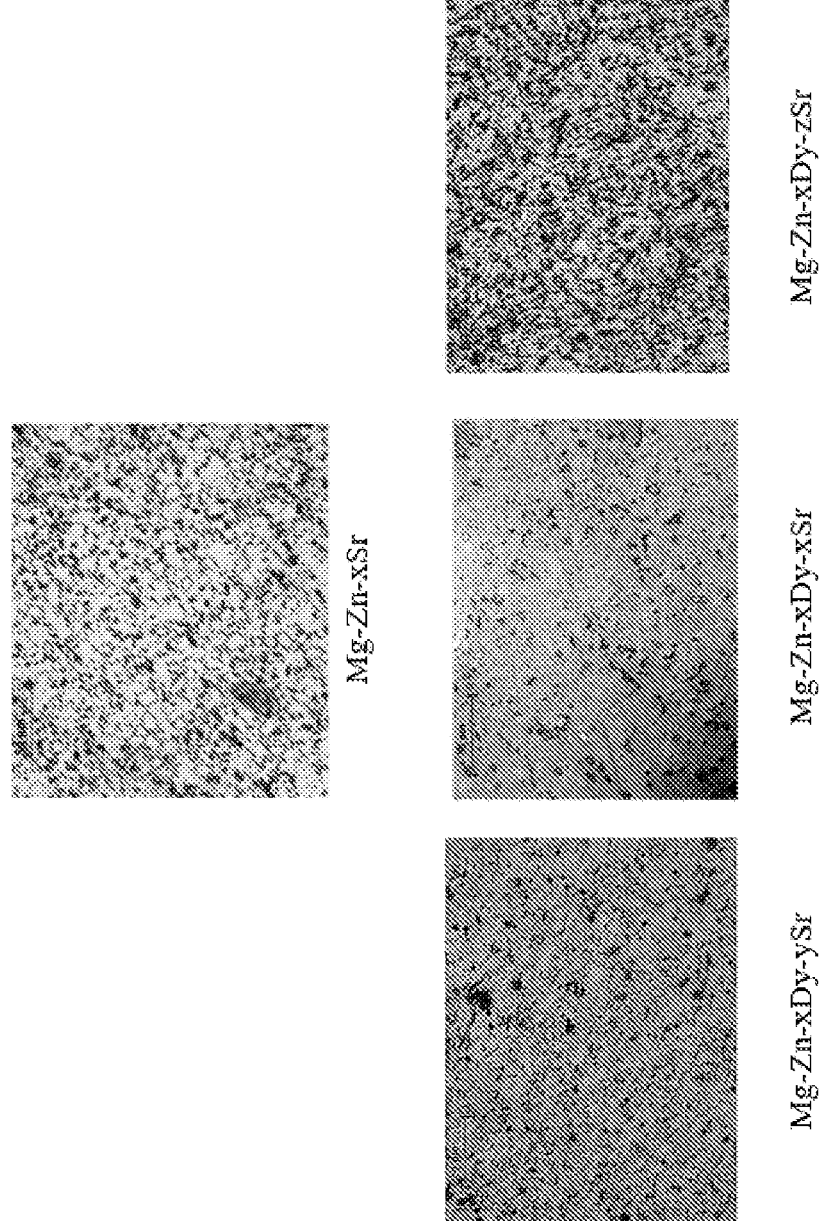

[Fig. 2]
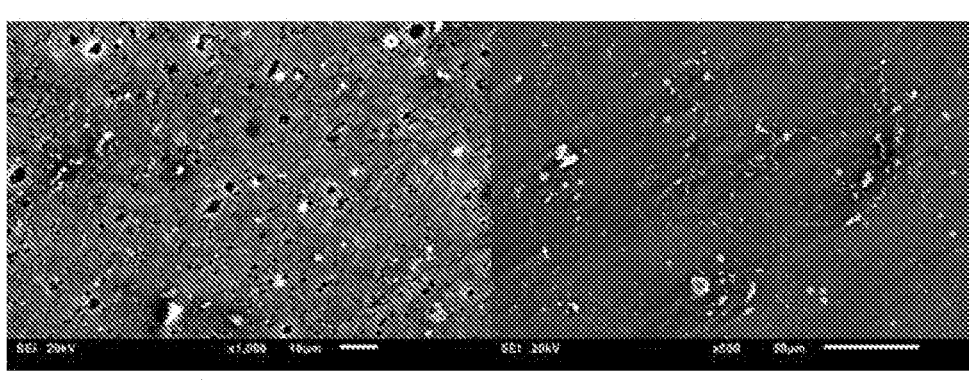
Mg-Zn-xSr                Mg-Zn-xDy-ySr
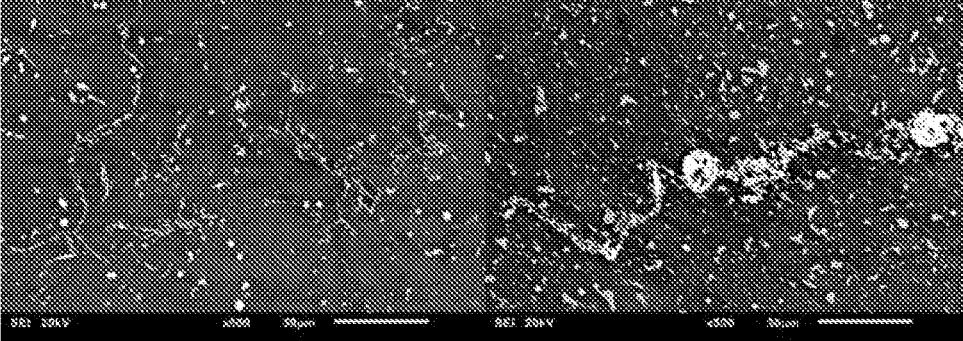
Mg-Zn-xDy-xSr            Mg-Zn-xDy-zSr

[Fig. 3]
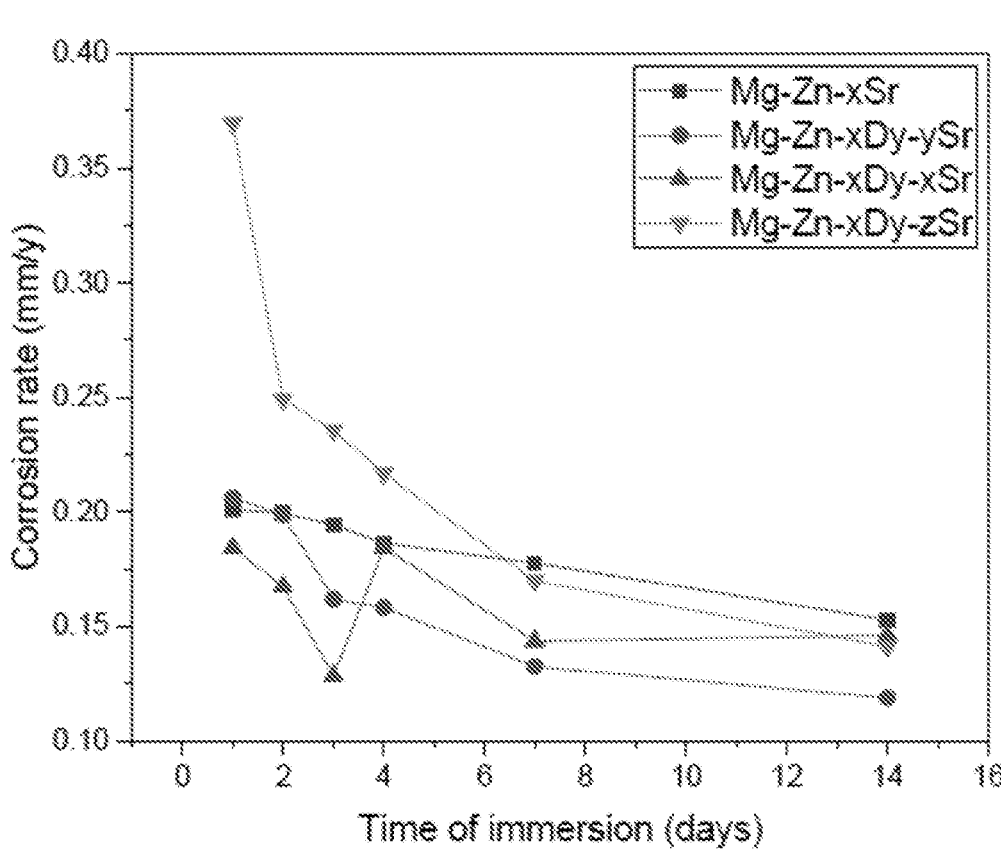

[Fig. 4A]
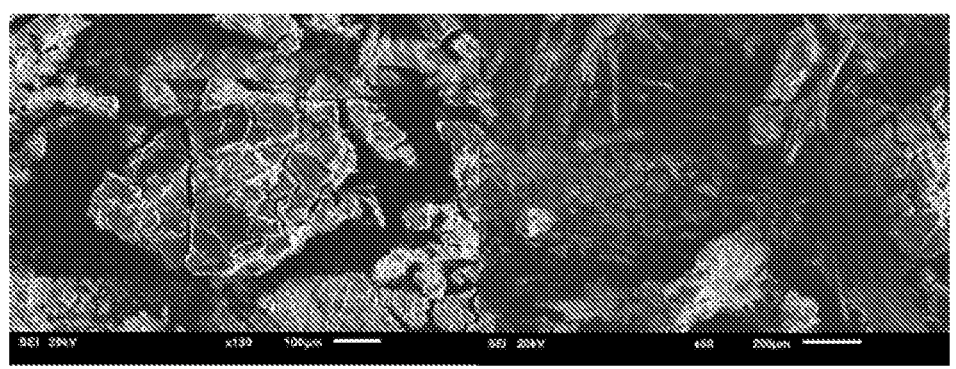
Mg-Zn-xSr           Mg-Zn-xDy-ySr
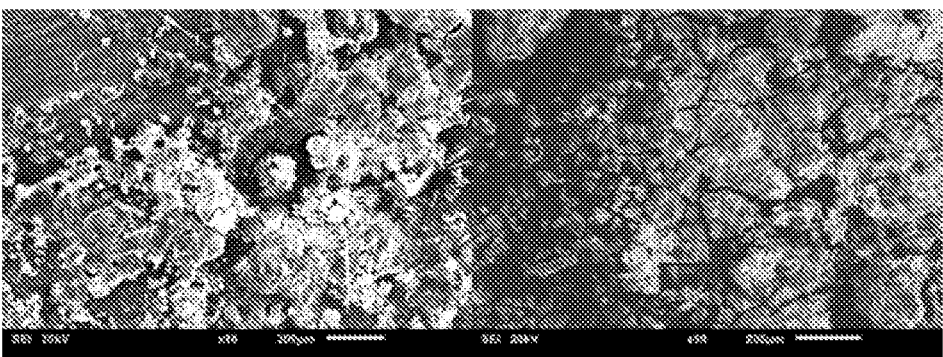
Mg-Zn-xDy-xSr        Mg-Zn-xDy-zSr

[Fig. 4B]
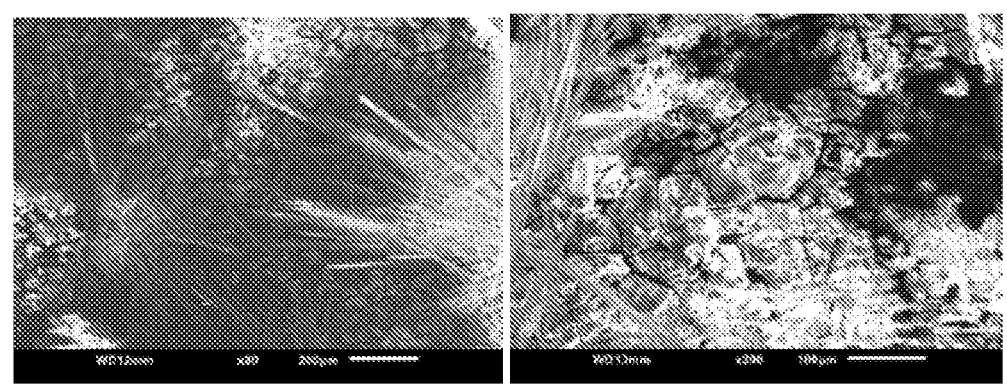
Mg-Zn-aCa-bMn                    Mg-Zn-aCa-cMn
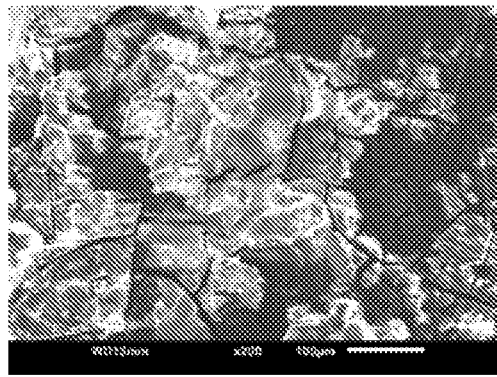
Mg-Zn-aCa-dMn

[Fig. 5A]
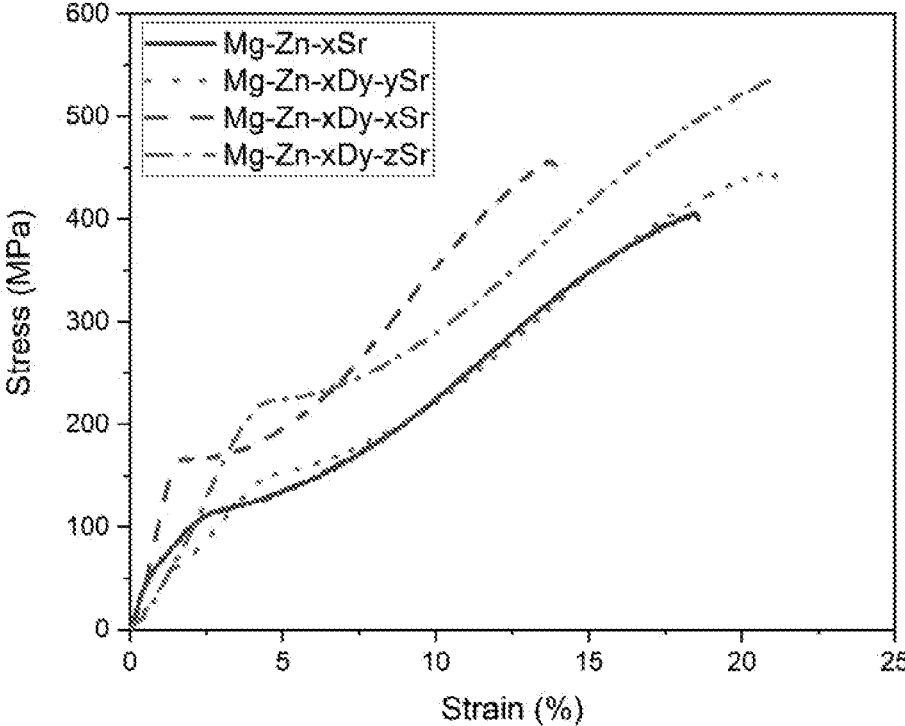
[Fig. 5B]
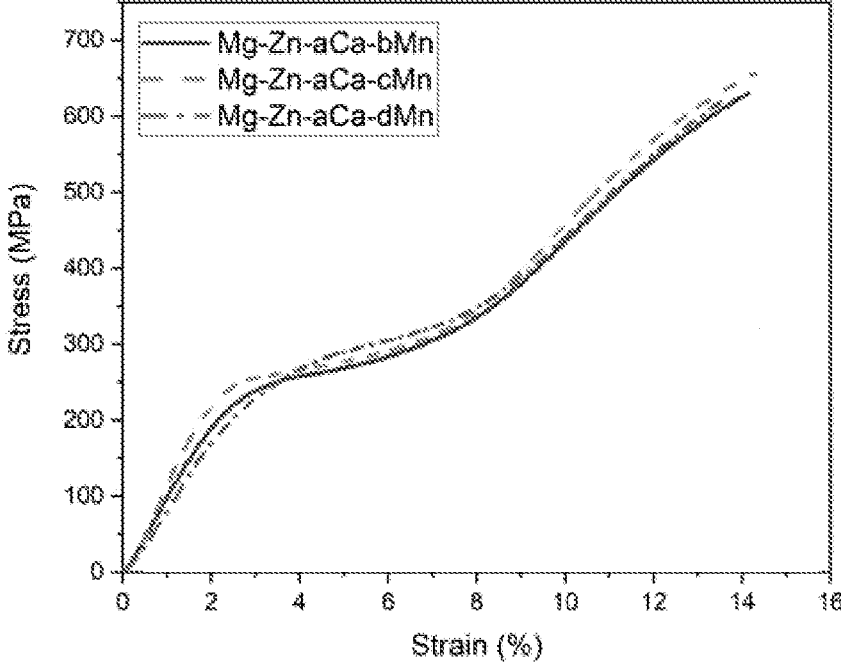

[Fig. 6A]
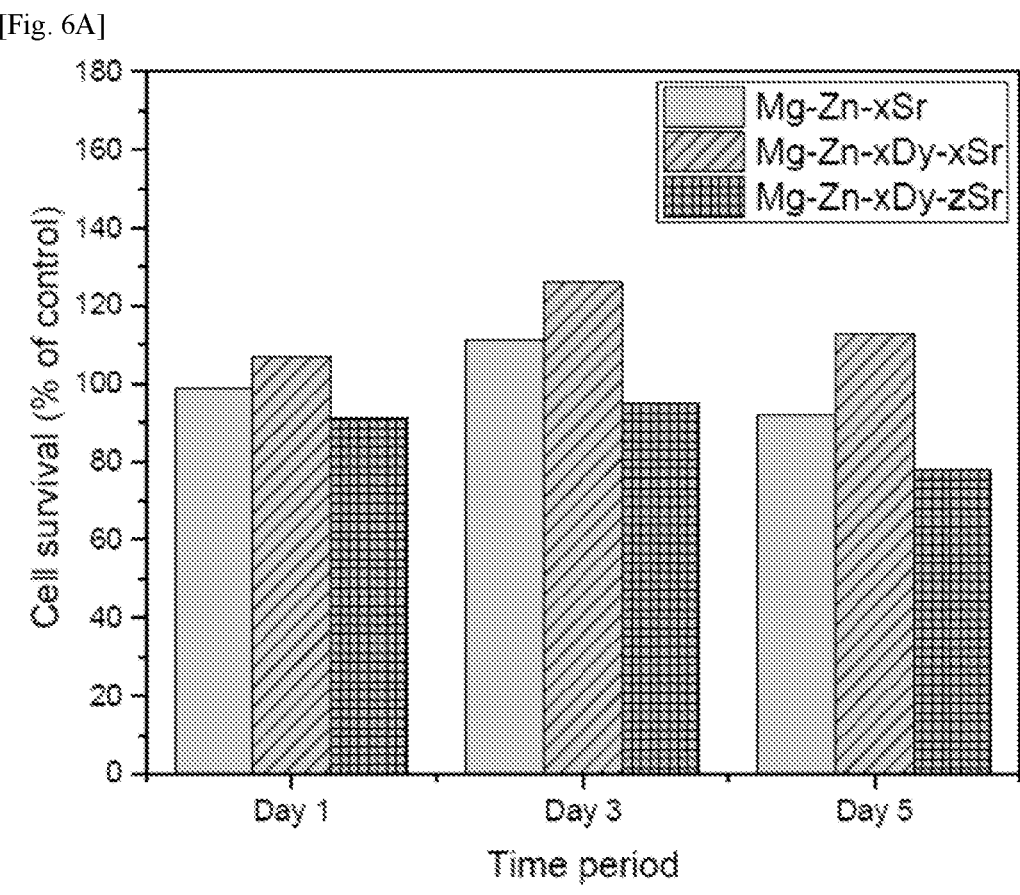
[Fig. 6B]
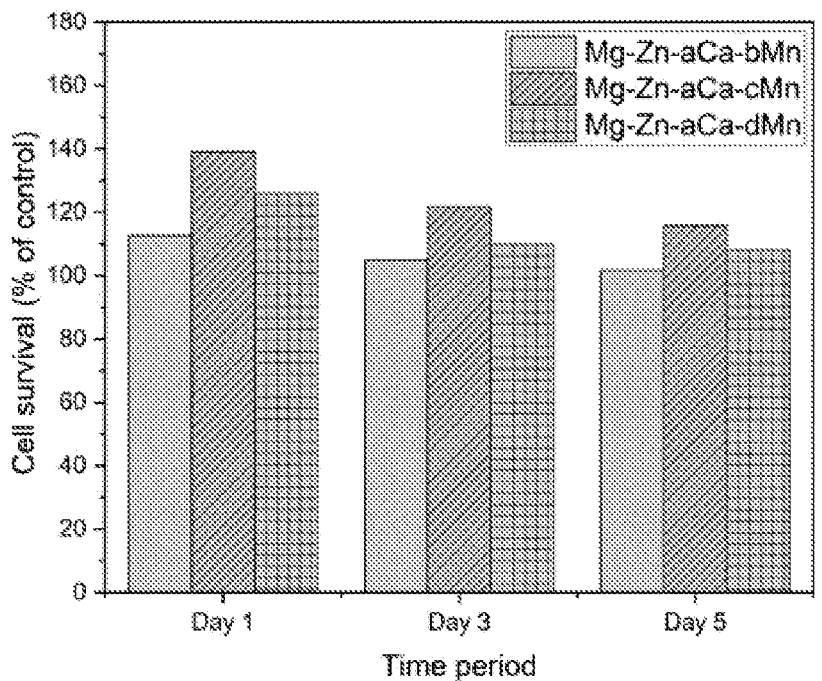

[Fig. 7]
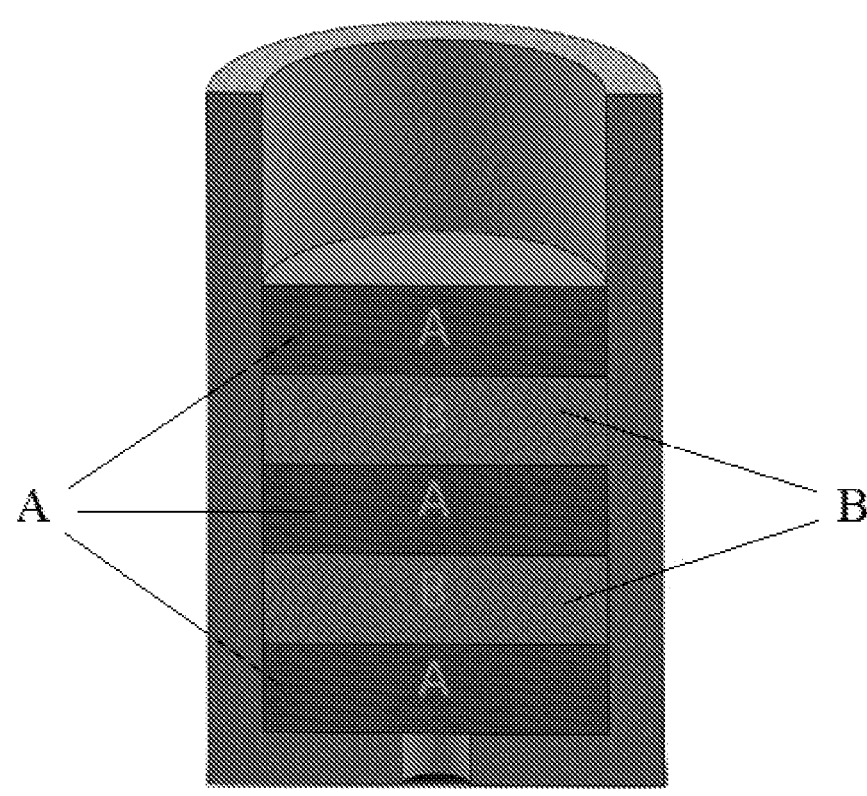

[Fig. 8A]
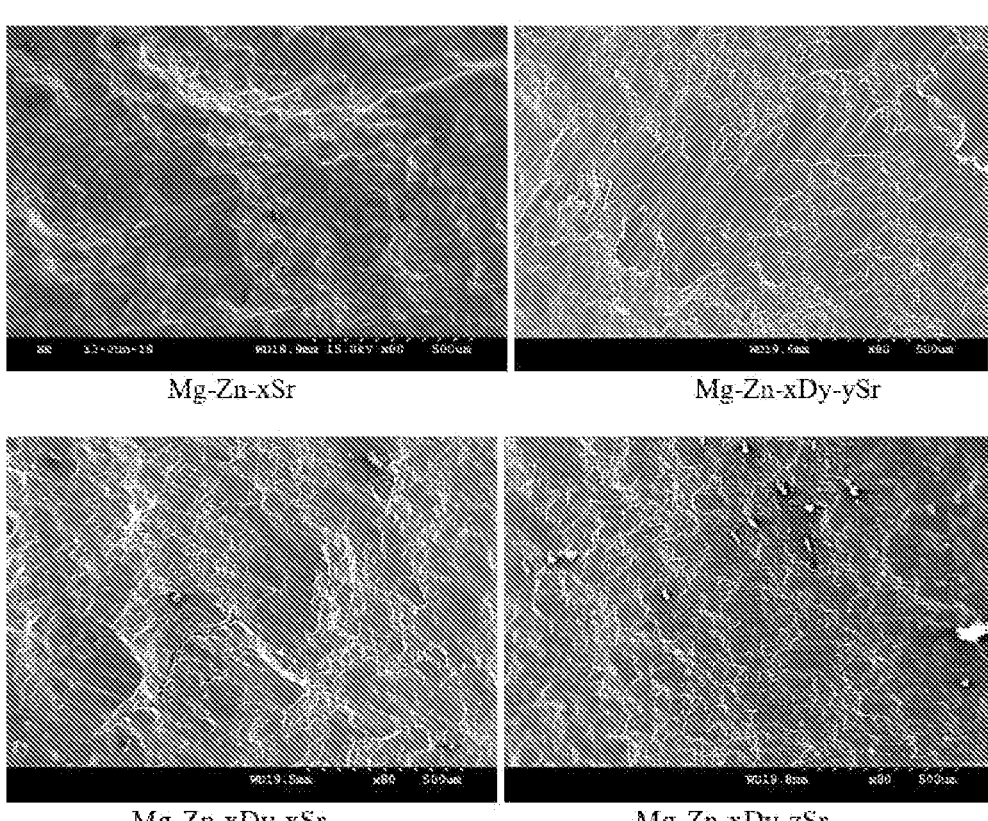
Mg-Zn-xSr             Mg-Zn-xDy-ySr
Mg-Zn-xDy-xSr          Mg-Zn-xDy-zSr

[Fig. 8B]
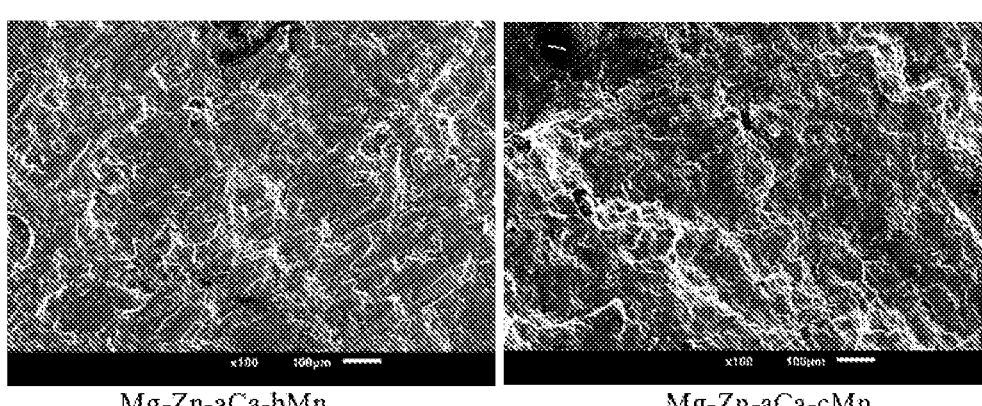
Mg-Zn-aCa-bMn                Mg-Zn-aCa-cMn
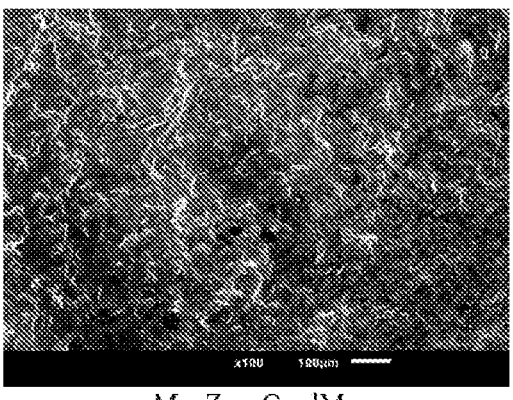
Mg-Zn-aCa-dMn

BIODEGRADABLE MAGNESIUM ALLOYS

TECHNICAL FIELD

The present invention generally relates to biodegradable alloys. The present invention also relates to processes and techniques for producing said biodegradable alloys. The biodegradable alloys may be useful in orthopedic applications.

BACKGROUND ART

With the world's aging population, the number of age-related orthopedic conditions, such as osteoporosis and fractures, have risen tremendously. This has in turn increased the demand for effective and inexpensive orthopedic implants and devices. Research and development is ongoing to search for the ideal orthopedic implant material. There are several factors (e.g. orthopedic application/area, function, suitability and cost) and properties of the material to be considered, such as chemical and bio-inertness, strength, rigidity, corrosion, stability, biocompatibility and tissue receptivity.

Currently, orthopedic implants and devices are manufactured using either polymer, ceramic or metallic materials. Each has its own strengths and limitations. Metallic materials, such as stainless steel, platinum, titanium, and alloys like titanium and chromium-cobalt alloys, are commonly used due to their excellent strength and mechanical properties. However, these metallic implants tend to be mismatched with the bone and may lead to the loosening of the implant and ultimately lead to implant failure. Therefore, these metallic implants may have to be removed after serving its healing purpose due to the possible complications of recovery (such as allergy, infections and sensitization).

As for polymers, polyethylene and polymethylmethacrylate are some common examples used for orthopedic implants. However, due to their low strength and possible deformation, they are not suitable for heavy load orthopedic applications (such as bone healing).

Ceramics such as aluminum oxide, silicon oxide, zirconium oxide and calcium phosphate possess good mechanical properties and are chemical- and biocompatibility. However, they are brittle.

Hence, there is a need to provide a suitable material for orthopedic applications that overcomes, or at least ameliorates, one or more of the disadvantages described above. The combination of properties such as chemical inertness, strength, rigidity, stability, biocompatibility, tissue receptivity and resistance to corrosion would make an ideal material for orthopedic implants and applications.

SUMMARY OF INVENTION

In one aspect of the present disclosure, there is provided a biodegradable alloy of Formula (I):

Mg—Zn—X                                    Formula (I)

wherein:
  X represents —Ca—Mn or —Dy—Sr;
  Mg is magnesium, Zn is zinc, Dy is dysprosium, Sr is
    strontium,
  Ca is calcium and Mn is manganese;
  wherein said alloy comprises, based on total alloy weight:
    about 0.1 wt % to about 3.0 wt % Zn;
    about 0.1 wt % to about 0.7 wt % Dy;
    about 0.1 wt % to about 0.9 wt % Sr;

about 0.1 wt % to about 1.5 wt % Ca;
    about 0.1 wt % to about 0.9 wt % Mn; and
    balance of Mg and impurities.

In another aspect of the present disclosure, there is provided an implant comprising the alloy disclosed herein.

Advantageously, the disclosed biodegradable alloys may possess zero level cytotoxicity which allows for the effective use of the material in orthopedic, neurosurgical, cranial, maxillofacial applications and lowers the associated risks to the patients.

Low weight fractions of alloying element (e.g. zinc) may be used in the biodegradable alloys. Advantageously, this lowers the cost of the alloy. Similarly with trace additions of biocompatible elements like calcium and manganese, or rare earth elements such as strontium and dysprosium, the cost of the biodegradable alloy may be kept low with all functions and properties met.

In a further aspect of the present disclosure, there is provided a method for producing an alloy comprising:
  (a) placing alloy components in a crucible, wherein the
      alloy components are placed in the crucible in a mul-
      tilayer arrangement;
  (b) melting the alloy components at about 700° C. to
      about 850° C.;
  (c) stirring the melt of step (b) at about 400 rpm to about
      500 rpm;
  (d) atomizing the melt of step (c) into millimeter size
      droplets using jets of inert gas;
  (e) cooling and depositing the atomized alloy melt to
      obtain an ingot.

In another aspect of the present disclosure, there is provided a method for producing an alloy of Formula (I):

Mg—Zn—X                                    Formula (I)

wherein:
  X represents —Ca—Mn or —Dy—Sr;
  Mg is magnesium, Zn is zinc, Dy is dysprosium, Sr is
    strontium, Ca is calcium and Mn is manganese;
  wherein said alloy comprises, based on total alloy weight:
    about 0.1 wt % to about 3.0 wt % Zn;
    about 0.1 wt % to about 0.7 wt % Dy;
    about 0.1 wt % to about 0.9 wt % Sr;
    about 0.1 wt % to about 1.5 wt % Ca;
    about 0.1 wt % to about 0.9 wt % Mn; and
    balance of Mg and impurities,
  wherein said method comprises:
  (a) placing alloy components in a crucible, wherein the
      alloy components are placed in the crucible in a mul-
      tilayer arrangement;
  (b) melting the alloy components at about 700° C. to
      about 850° C.;
  (c) stirring the melt of step (b) at about 400 rpm to about
      500 rpm;
  (d) atomizing the melt of step (c) into millimeter size
      droplets using jets of inert gas;
  (e) cooling and depositing the atomized alloy melt to
      obtain an ingot.

Advantageously, arranging the alloy components in this multilayer or sandwich fashion ensures the maximum capture and wettability of the alloy matrix material (which may be the first alloy component) as the alloying element(s) in the second alloy component may have different melting points as compared to the alloy matrix material. This layerwise or multilayer arrangement ensures the best possible homogenization of the alloying elements into the molten matrix metal/material.

Using the disclosed methods of the present invention, the disclosed biodegradable alloy can be manufactured effectively without using any toxic flux materials and protective gases like sulfur hexafluoride. Therefore advantageously, the production of the disclosed biodegradable alloy is a safe, cost effective, energy-efficient and industrially scalable process. The disclosed biodegradable alloy and disclosed method for forming alloys may be able to meet the high demand of materials required for orthopedic implants and devices (e.g. temporary implants for neurosurgical, cranial, maxillofacial and orthopedic fracture, fixation applications, used for bioresorbable screws, plates, pins and clips).

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

Unless the context requires otherwise or specifically stated to the contrary, integers, steps, or elements of the invention recited herein as singular integers, steps or elements clearly encompass both singular and plural forms of the recited integers, steps or elements.

As used herein, the term "bioresorbable" refers that it can be broken down, degraded and absorbed by the body and thus does not need to be removed manually. It is also known as biodegradable.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.
FIG. 1
FIG. 1 shows the grain size morphology of magnesium alloys of the present invention studied under an optical microscope.
FIG. 2
FIG. 2 shows the optical micrograph analysis of the magnesium alloys.
FIG. 3
FIG. 3 shows the corrosion rate of the magnesium alloys.
FIGS. 4A and 4B
FIG. 4A shows the scanning electron microscope (SEM) analysis of post-corroded magnesium alloys Mg—Zn-xSr, Mg—Zn-xDy-ySr, Mg—Zn-xDy-xSr, Mg—Zn-xDy-zSr, at the end of 14 days. FIG. 4B shows the scanning electron microscope (SEM) analysis of post-corroded magnesium alloys Mg—Zn-aCa, Mg—Zn-aCa-cMn, Mg—Zn-aCa-dMn at the end of 14 days.
FIGS. 5A and 5B
FIG. 5A shows the compression properties of magnesium alloys Mg—Zn-xSr, Mg—Zn-xDy-ySr, Mg—Zn-xDy-xSr, Mg—Zn-xDy-zSr. FIG. 5B shows the compression properties of magnesium alloys Mg—Zn-aCa, Mg—Zn-aCa-cMn, Mg—Zn-aCa-dMn.
FIGS. 6A and 6B
FIG. 6A shows the cell viability of MC3T3-E1 pre-osteoblast cells expressed as a percentage of the viability of cells cultured in negative control after incubating magnesium alloys Mg—Zn-ySr, Mg—Zn-xDy-xSr, and Mg—Zn-xDy-zSr for 1, 3, and 5 days. FIG. 6B shows the cell viability of MC3T3-E1 pre-osteoblast cells expressed as a percentage of the viability of cells cultured in the negative control after incubating magnesium alloys Mg—Zn-aCa, Mg—Zn-aCa-cMn, and Mg—Zn-aCa-dMn for 1, 3, and 5 days.
FIG. 7
FIG. 7 is a cross-section schematic of the crucible showing the multilayer arrangement of the alloy components.
FIGS. 8A and 8B
FIG. 8A shows post compressive fractured samples of magnesium alloys Mg—Zn-xSr, Mg—Zn-xDy-ySr, Mg—Zn-xDy-xSr, Mg—Zn-xDy-zSr. FIG. 8B shows post compressive fractured samples of magnesium alloys Mg—Zn-aCa, Mg—Zn-aCa-cMn, and Mg—Zn-aCa-dMn.

DETAILED DESCRIPTION OF DRAWINGS

Referring to FIGS. 4A and 4B, FIGS. 4A and 4B show the scanning electron microscope (SEM) analysis of post-corroded magnesium alloys at the end of 14 days. The magnesium alloys display a crack formation due to water loss. The alloy surfaces are covered by needle-like structures. The formation of the brucite compound is intensified with increased immersion time of the magnesium alloys in Hank's balanced salt solution (HBSS). The extent of compound formation was more evenly distributed in the alloy samples. This behavior can assist in the strength and ductility retention of the material post in vitro corrosion.

Referring to FIGS. 5A and 5B, FIGS. 5A and 5B show the compression properties of the magnesium alloys. FIGS. 5A and 5B show the stress against strain graph or compressive testing of the magnesium alloys and provides more insight on the mechanical integrity of the alloys. Based on FIGS. 5A and 5B, the amount of strength retained by the material post-implantation can be assessed and the functional life cycle requirements of the implant can be determined.

Referring to FIGS. 8A and 8B, FIGS. 8A and 8B show the fracture morphology of the magnesium alloys after compression testing which provides insights on the mechanism of failure and the amount of energy absorbed by the implant before failure.

DETAILED DISCLOSURE OF EMBODIMENTS

Magnesium is non-toxic, biocompatible, bioresorbable, of low density and possesses mechanical properties closer to that of bone. However, monolithic magnesium displays low corrosion resistance in physiological environments leading to low mechanical properties retention and possible implant failure prior to complete bone repair. Modification of magnesium using an alloying technology is crucial in order to tailor the properties to meet that of an ideal orthopedic implant material.

In the present invention, suitable alloying elements like zinc and biocompatible elements like dysprosium, strontium, calcium and manganese are used in optimized amounts in the magnesium matrix to develop unique biodegradable magnesium-based alloys with improved mechanical, degradation and cytotoxicity response.

The present disclosure relates to a biodegradable alloy of Formula (I):

$$Mg—Zn—X \qquad \text{Formula (I)}$$

wherein:
  X represents —Ca—Mn or —Dy—Sr;
  Mg is magnesium, Zn is zinc, Dy is dysprosium, Sr is strontium, Ca is calcium and Mn is manganese;
  wherein said alloy comprises or consists of, based on total alloy weight:
   about 0.1 wt % to about 3.0 wt % Zn;
   about 0.1 wt % to about 0.7 wt % Dy;
   about 0.1 wt % to about 0.9 wt % Sr;
   about 0.1 wt % to about 1.5 wt % Ca;
   about 0.1 wt % to about 0.9 wt % Mn; and
   balance of Mg and impurities.

The biodegradable alloy may be of Formula (IA): Mg—Zn—Ca—Mn.

The biodegradable alloy may be of Formula (IB): Mg—Zn—Dy—Sr.

The alloy may comprise zinc at about 0.1 wt % to about 3.0 wt %, about 0.2 wt % to about 3.0 wt %, about 0.3 wt % to about 3.0 wt %, about 0.4 wt % to about 3.0 wt %, about 0.5 wt % to about 3.0 wt %, about 0.6 wt % to about 3.0 wt %, about 0.7 wt % to about 3.0 wt %, about 0.8 wt % to about 3.0 wt %, about 0.9 wt % to about 3.0 wt %, about 1.0 wt % to about 3.0 wt %, about 1.1 wt % to about 3.0 wt %, about 1.2 wt % to about 3.0 wt %, about 1.3 wt % to about 3.0 wt %, about 1.4 wt % to about 3.0 wt %, about 1.5 wt % to about 3.0 wt %, about 1.6 wt % to about 3.0 wt %, about 1.7 wt % to about 3.0 wt %, about 1.8 wt % to about 3.0 wt %, about 1.9 wt % to about 3.0 wt %, about 2.0 wt % to about 3.0 wt %, about 2.0 wt % to about 2.5 wt % to about 2.1 wt % to about 2.2 wt %, about 2.3 wt % to about 3.0 wt %, about 2.4 wt % to about 3.0 wt %, about 2.5 wt % to about 3.0 wt %, about 2.6 wt % to about 3.0 wt %, about 2.7 wt % to about 3.0 wt %, about 2.8 wt % to about 3.0 wt %, about 2.9 wt % to about 3.0 wt %, about 0.1 wt % to about 2.9 wt %, about 0.1 wt % to about 2.8 wt %, about 0.1 wt % to about 2.7 wt %, about 0.1 wt % to about 2.6 wt %, about 0.1 wt % to about 2.5 wt %, about 0.1 wt % to about 2.4 wt %, about 0.1 wt % to about 2.3 wt %, about 0.1 wt % to about 2.2 wt %, about 0.1 wt % to about 2.1 wt %, about 0.1 wt % to about 2.0 wt %, about 0.1 wt % to about 1.9 wt %, about 0.1 wt % to about 1.8 wt %, about 0.1 wt % to about 1.7 wt %, about 0.1 wt % to about 1.6 wt %, about 0.1 wt % to about 1.5 wt %, about 0.1 wt % to about 1.4 wt %, about 0.1 wt % to about 1.3 wt %, about 0.1 wt % to about 1.2 wt %, about 0.1 wt % to about 1.1 wt %, about 0.1 wt % to about 1.0 wt %, about 0.1 wt % to about 0.9 wt %, about 0.1 wt % to about 0.8 wt %, about 0.1 wt % to about 0.7 wt %, about 0.1 wt % to about 0.6 wt %, about 0.1 wt % to about 0.5 wt %, about 0.1 wt % to about 0.4 wt %, about 0.1 wt % to about 0.3 wt %, about 0.1 wt % to about 0.2 wt %, or may comprise zinc at about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, or any value or range therebetween.

The alloy may comprise calcium at about 0.1 wt % to about 1.5 wt %, about 0.2 wt % to about 1.5 wt %, about 0.3 wt % to about 1.5 wt %, about 0.4 wt % to about 1.5 wt %, about 0.5 wt % to about 1.5 wt %, about 0.5 wt % to about 1.0 wt %, about 0.6 wt % to about 1.5 wt %, about 0.7 wt % to about 1.5 wt %, about 0.8 wt % to about 1.5 wt %, about 0.9 wt % to about 1.5 wt %, about 1.0 wt % to about 1.5 wt %, about 1.1 wt % to about 1.5 wt %, about 1.2 wt % to about 1.5 wt %, about 1.3 wt % to about 1.5 wt %, about 1.4 wt % to about 1.5 wt %, about 0.1 wt % to about 1.4 wt %, about 0.1 wt % to about 1.3 wt %, about 0.1 wt % to about 1.2 wt %, about 0.1 wt % to about 1.1 wt %, about 0.1 wt % to about 1.0 wt %, about 0.1 wt % to about 0.9 wt %, about 0.1 wt % to about 0.8 wt %, about 0.1 wt % to about 0.7 wt %, about 0.1 wt % to about 0.6 wt %, about 0.1 wt % to about 0.5 wt %, about 0.1 wt % to about 0.4 wt %, about 0.1 wt % to about 0.3 wt %, about 0.1 wt % to about 0.2 wt %, or may comprise calcium at about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, or any value or range therein.

The alloy may comprise manganese at about 0.1 wt % to about 0.9 wt %, about 0.2 wt % to about 0.9 wt %, about 0.2 wt % to about 0.8 wt %, about 0.3 wt % to about 0.9 wt %, about 0.4 wt % to about 0.9 wt %, about 0.5 wt % to about 0.9 wt %, about 0.6 wt % to about 0.9 wt %, about 0.7 wt % to about 0.9 wt %, about 0.8 wt % to about 0.9 wt %, about 0.1 wt % to about 0.8 wt %, about 0.1 wt % to about 0.7 wt %, about 0.1 wt % to about 0.6 wt %, about 0.1 wt % to about 0.5 wt %, about 0.1 wt % to about 0.4 wt %, about 0.1 wt % to about 0.3 wt %, about 0.1 wt % to about 0.2 wt %, or may comprise manganese at about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or any value or range therein.

The alloy may comprise dysprosium at about 0.1 wt % to about 0.7 wt %, about 0.2 wt % to about 0.7 wt %, about 0.3 wt % to about 0.7 wt %, about 0.4 wt % to about 0.7 wt %, about 0.4 wt % to about 0.6 wt %, about 0.5 wt % to about 0.7 wt %, about 0.6 wt % to about 0.7 wt %, about 0.1 wt % to about 0.6 wt %, about 0.1 wt % to about 0.5 wt %, about 0.1 wt % to about 0.4 wt %, about 0.1 wt % to about 0.3 wt %, about 0.1 wt % to about 0.2 wt %, or may comprise dysprosium at about 0.1 wt %, about 0.2 wt %, about 0.3 wt %, about 0.4 wt %, about 0.5 wt %, about 0.6 wt %, about 0.7 wt %, or any value or range therein.

The alloy may comprise strontium at about 0.1 wt % to about 0.9 wt %, about 0.2 wt % to about 0.9 wt %, about 0.2 wt % to about 0.8 wt %, about 0.3 wt % to about 0.9 wt %, about 0.4 wt % to about 0.9 wt %, about 0.5 wt % to about 0.9 wt %, about 0.6 wt % to about 0.9 wt %, about 0.7 wt % to about 0.9 wt %, about 0.8 wt % to about 0.9 wt %, about 0.1 wt % to about 0.8 wt %, about 0.1 wt % to about 0.7 wt %, about 0.1 wt % to about 0.6 wt %, about 0.1 wt % to about 0.5 wt %, about 0.1 wt % to about 0.4 wt %, about 0.1 wt % to about 0.3 wt %, about 0.1 wt % to about 0.2 wt %, or may comprise strontium at about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or any value or range therein.

The biodegradable alloy may be selected from the group consisting of:

Mg—Zn—Ca—Mn, wherein Zn is 2.5 wt %, Ca is 1.0 wt %, Mn is 0.3 wt % and Mg makes up the balance;

Mg—Zn—Ca—Mn, wherein Zn is 2.5 wt %, Ca is 1.0 wt %, Mn is 0.5 wt % and Mg makes up the balance;

Mg—Zn—Ca—Mn, wherein Zn is 2.5 wt %, Ca is 1.0 wt %, Mn is 0.7 wt % and Mg makes up the balance.

Mg—Zn—Dy—Sr, wherein Zn is 2.5 wt %, Dy is 0.5 wt %, Sr is 0.2 wt % and Mg makes up the balance;

Mg—Zn—Dy—Sr, wherein Zn is 2.5 wt %, Dy is 0.5 wt %, Sr is 0.5 wt % and Mg makes up the balance; and Mg—Zn—Dy—Sr, wherein Zn is 2.5 wt %, Dy is 0.5 wt %, Sr is 0.8 wt % and Mg makes up the balance.

The alloy may comprise trace amounts of impurities, such as aluminum, iron, nickel, silicon or copper. Each impurity or the total amount of impurities may constitute about 20 ppm or less, or about 20 ppm, about 19 ppm, about 18 ppm, about 17 ppm, about 16 ppm, about 15 ppm, about 14 ppm, about 13 ppm, about 12 ppm, about 11 ppm, about 10 ppm, about 9 ppm, about 8 ppm, about 7 ppm, about 6 ppm, about 5 ppm, about 4 ppm, about 3 ppm, about 2 ppm, about 1 ppm, or about 0 ppm.

The alloy may advantageously not contain yttrium which is known to be cytotoxic. The inventors have surprisingly found that yttrium may be omitted from the alloy and by using trace additions of strontium, calcium, manganese and dysprosium instead, similar functional advantages may be achieved with lower risk and lower costs.

The present disclosure also relates to an implant comprising a biodegradable alloy of Formula (I):

Mg—Zn—X    Formula (I)

wherein:

X represents —Ca—Mn or —Dy—Sr;

Mg is magnesium, Zn is zinc, Dy is dysprosium, Sr is strontium, Ca is calcium and Mn is manganese;

wherein said alloy comprises or consists of, based on total alloy weight:

about 0.1 wt % to about 3.0 wt % Zn;

about 0.1 wt % to about 0.7 wt % Dy;

about 0.1 wt % to about 0.9 wt % Sr;

about 0.1 wt % to about 1.5 wt % Ca;

about 0.1 wt % to about 0.9 wt % Mn; and balance of Mg and impurities.

The implant may be an orthopedic, cranial, maxillofacial, neurosurgical or dental implant.

The present disclosure further relates to a method for producing an alloy comprising:

(a) placing alloy components in a crucible, wherein the alloy components are placed in the crucible in a multilayer arrangement;

(b) melting the alloy components at about 700° C. to about 850° C.;

(c) stirring the melt of step (b) at about 400 rpm to about 500 rpm;

(d) atomizing the melt of step (c) into millimeter size droplets using jets of inert gas;

(e) cooling and depositing the atomized alloy melt to obtain an ingot.

The present disclosure further relates to a method for producing an alloy of Formula (I):

Mg—Zn—X    Formula (I)

wherein:

X represents —Ca—Mn or —Dy—Sr;

Mg is magnesium, Zn is zinc, Dy is dysprosium, Sr is strontium, Ca is calcium and Mn is manganese;

wherein said alloy comprises or consists of, based on total alloy weight:

about 0.1 wt % to about 3.0 wt % Zn;

about 0.1 wt % to about 0.7 wt % Dy;

about 0.1 wt % to about 0.9 wt % Sr;

about 0.1 wt % to about 1.5 wt % Ca;

about 0.1 wt % to about 0.9 wt % Mn; and

Balance of Mg and impurities, wherein said method comprises:

(a) placing alloy components in a crucible, wherein the alloy components are placed in the crucible in a multilayer arrangement;

(b) melting the alloy components at about 700° C. to about 850° C.;

(c) stirring the melt of step (b) at about 400 rpm to about 500 rpm;

(d) atomizing the melt of step (c) into millimeter size droplets using jets of inert gas;

(e) cooling and depositing the atomized alloy melt to obtain an ingot.

The crucible may be a graphite or metal crucible.

Step (a) may comprise controlling the volume of the alloy components to about 70% to about 75% the volume of the crucible. The inventors have surprisingly found that when the volume of precursor material/alloy components is controlled in the range of about 70% to about 75% with respect to the volume of the crucible, the molten flow rate is regulated for the amount of material used as the raw material. This engineering control advantageously ensures the reproducibility of the deposited material into the mold. Furthermore, with the uniform molten metal flow rate, the amount of gas impinging on the downpouring molten metal is also standardized, further regulating the heat extraction from the molten metal stream. The controlled volume of inert gas impingement into the molten metal stream standardizes the volume ratio of gas and molten metal thus advantageously ensuring reproducibility of similar microstructure evolution and mechanical properties of the deposited material.

The volume of the alloy components may be about 70%, about 71%, about 72%, about 73%, about 74%, or about 75% the volume of the crucible.

Additionally, in step (a), the multilayer arrangement of step (a) may comprise an A-B-A arrangement, wherein A comprises or consists of a first alloy component and B comprises or consists of a second alloy component, wherein the first and second alloy components may each comprise or consist of a single alloy material or a blended alloy mixture of two or more alloy materials.

The inventors have surprisingly found that arranging the alloy components in this multilayer or sandwich fashion ensures the maximum capture and wettability of the alloy matrix material (which may be the first alloy component) as the alloying element(s) in the second alloy component may have different melting points as compared to the alloy matrix material. This layerwise or multilayer arrangement ensures the best possible homogenization of the alloying elements into the molten matrix metal/material.

In another embodiment, the multilayer arrangement of step (a) may comprise an A-B-A-B-A arrangement, wherein A comprises or consists of a first alloy component and B comprises or consists of a second alloy component, wherein the first and second alloy components may each comprise or consist of a single alloy material or a blended alloy mixture of two or more alloy materials.

FIG. 7 is a cross-section schematic of the crucible showing the multilayer arrangement. (A) refers to the first alloy component layer, and (B) refers to the second alloy component layer.

In an embodiment, A may consist of magnesium and B may consist of a blended alloy mixture of zinc and X.

In an embodiment, A may consist of magnesium and B may consist of a blended alloy mixture of zinc, calcium, and manganese.

In an embodiment, A may consist of magnesium and B may consist of a blended alloy mixture of zinc, dysprosium and strontium.

Each layer of the multilayer arrangement may be of substantially equal volume. Advantageously, this assists in uniform heating of each layer within the furnace.

The inventors have surprisingly found that arranging the alloy components in this multilayer or sandwich fashion ensures the maximum capture and wettability of the magnesium matrix as the alloying element(s) (such as zinc, manganese, calcium, dysprosium and strontium) may have different melting points as compared to magnesium. Magnesium, in the form of turnings, may be arranged in three equal volume layers with the blended alloy layer mixture sandwiched between the magnesium layers. Post melting of magnesium, this layerwise/multilayer arrangement advantageously ensures the best possible homogenization of the alloying elements into the molten magnesium metal.

The method of the present invention is a liquid based processing methodology. Magnesium may be the matrix material, and the constituent elements (such as zinc, manganese, calcium, dysprosium and strontium) may be added to the crucible with the magnesium in a multilayer or sandwich arrangement. As the constituent elements are in low weight percentage, using a multilayer or sandwich arrangement advantageously ensures a proper pre-mixing of these constituent elements with the magnesium which may be in the form of magnesium turnings. The morphology of constituent elements may be in powder, ingot shot or wire form. Considering the different possibilities, the multilayer or sandwich arrangement provides the best uniformity while stirring and pouring and subsequently in the final cast.

Step (b) may be performed at a temperature of about 700° C. to about 850° C., about 725° C. to about 850° C., about 750° C. to about 850° C., about 775° C. to about 850° C., about 800° C. to about 850° C., about 825° C. to about 850° C., about 700° C. to about 825° C., about 700° C. to about 800° C., about 700° C. to about 775° C., about 700° C. to about 750° C., about 700° C. to about 725° C., or about 700° C., about 725° C., about 750° C., about 775° C., about 800° C., about 825° C., about 850° C., or any value or range therein.

The stirring in step (c) may be performed at about 400 rpm to about 500 rpm, about 425 rpm to about 450 rpm, about 450 rpm to about 500 rpm, about 475 rpm to about 500 rpm, about 400 rpm to about 475 rpm, about 400 rpm to about 450 rpm, about 400 rpm to about 425 rpm, or about 400 rpm, about 425 rpm, about 450 rpm, about 475 rpm, about 500 rpm, or any value or range therein.

The rate of the chosen stirring speed advantageously allows for uniform dispersion of the secondary phase particles in the melt. The optimized stirring speeds avoids agglomeration in the melt and the constituent elements are thoroughly mixed in the molten or semi-solid form. In the disclosed method, the alloy components are introduced in a sandwiched or multilayer form. Hence, optimized stirring advantageously improves the wettability of the first alloy component with the second alloy component.

The jets of inert gas in step (d) may be jets of nitrogen or argon. The number of jets used may be 2, 3 4, 5, or 6 jets. The diameter of each jet nozzle may be about 1 mm to about 2 mm and the gas flow rate may be about 20 L/min to about 30 L/min. The number of gas jets and gas flow rate may be adjusted so as to disintegrate the melt into millimeter size droplets. Flow rates and the number of jets affects the disintegration of the molten metal while it is bottom poured into the mold. Optimizing these parameters assists in higher wettability and the chemical and thermal homogenization of the molten metal during the deposition process.

The diameter of each jet nozzle may be about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. The gas flow rate may be about 20 L/min, about 2120 L/min, about 22 L/min, about 23 L/min, about 24 L/min, about 25 L/min, about 26 L/min, about 27 L/min, about 28 L/min, about 29 L/min, or about 30 L/min.

In step (d) the droplets may be millimeter size. The volume of each droplet may be about 1 mm$^3$, about 2 mm$^3$, about 3 mm$^3$, about 4 mm$^3$, about 5 mm$^3$, about 6 mm$^3$, about 7 mm$^3$, about 8 mm$^3$, or about 9 mm$^3$.

The method may further comprise step (f) subjecting the ingot to hot extrusion at about 250° C. to about 400° C. The temperature may be in the range of about 250° C. to about 400° C., about 275° C. to about 400° C., about 300° C. to about 400° C., about 325° C. to about 400° C., about 350° C. to about 400° C., about 375° C. to about 400° C., about 250° C. to about 375° C., about 250° C. to about 350° C., about 250° C. to about 325° C., about 250° C. to about 300° C., about 250° C. to about 275° C., or about 250° C., about 275° C., about 300° C., about 325° C., about 350° C., about 375° C., about 400° C., or any value or range therein.

The hot extrusion step may be performed for about 1 hour to about 2 hours, or about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

The extrusion ratio may be in the range of 25:1 to 12:1, or 24:1, 23:1, 23:1, 22:1, 21:1, 20:1, 19:1, 18:1, 17:1, 16:1, 15:1, 14:1, 13:1, or 12:1.

EXAMPLES

Non-limiting examples of the invention and a comparative example will be further described in greater detail by reference to specific Examples, which should not be construed as in any way limiting the scope of the invention.

Example 1: Synthesis of Magnesium Alloys

The raw materials were arranged in a multilayer sandwich form in a graphite crucible of 140 mm diameter and 200 m in length and melted in a temperature range of 700-850° C. (depending on composition) in a controlled argon gas environment. For uniform dispersion of the secondary phase particles in the melt, stirring conditions were optimized in the range of 400-500 rpm. The molten metal was then bottom poured into a steel mold and disintegrated by 2-4 circular jets of argon gas with 1-2 mm gas jet diameter and a gas flow rate of 20-30 L/m (liters per minute). The number of gas jets and the flow rate was optimized so as to disintegrate the melt in millimeter size droplets. Cast ingots of 40 mm diameter was obtained following the deposition and solidification of these millimeter size droplets (controlled volume in $mm^3$). This cast ingot was machined to specific dimensions, soaked at 300-400° C. for 1-2 hours and hot extruded at 250-400° C. at an extrusion ratio range of 25:1 to 12:1 yielding rods in the diameter range of 7-10 mm depending on composition. The cylindrical rods were used for various characterizations. The weight % of Mg, Zn, Dy, Sr, Ca and Mn in the magnesium alloys are shown in Table 1.

TABLE 1

|  | Weight % | | | | | |
| Notation | Mg | Zn | Dy | Sr | Ca | Mn |
| --- | --- | --- | --- | --- | --- | --- |
| Mg—Zn | Bal | 2.5 | — | — | — | — |
| Mg—Zn—xSr | Bal | 2.5 | — | 0.5 | — | — |
| Mg—Zn—xDy—ySr | Bal | 2.5 | 0.5 | 0.2 | — | — |
| Mg—Zn—xDy—xSr | Bal | 2.5 | 0.5 | 0.5 | — | — |
| Mg—Zn—xDy—zSr | Bal | 2.5 | 0.5 | 0.8 | — | — |
| Mg—Zn—aCa—bMn | Bal | 2.0 | — | — | 1.0 | 0.3 |
| Mg—Zn—aCa—cMn | Bal | 2.0 | — | — | 1.0 | 0.5 |
| Mg—Zn—aCa—dMn | Bal | 2.0 | — | — | 1.0 | 0.7 |

Example 2: Microstructural Characterization of Magnesium Alloys

Microstructural characterization was performed to calculate the average grain size and to characterize the distribution of secondary phases in the magnesium alloy matrix.

Analysis of Average Grain Size of Magnesium Alloys

According to Standard Test Methods for Determining Average Grain Size, (ASTM E112-13), the samples were examined under the digital optical microscope with LES 4.0 software to investigate the grain distribution. JEOL JSM-5800 LV Scanning Electron Microscope (SEM, Kyoto, Japan) was used for investigating the distribution of secondary phases.

The samples were immersed for 14 days in Hank's balanced salt solution (HBSS) procured from Lonza Chemicals Pte Ltd. Singapore. The Falcon tube was filled with the requisite amount of HBSS and the tube was kept in a water bath that was maintained at 37° C. to simulate the temperature of the human body. Weight loss and pH measurements were measured after days 1, 2, 3, 4, 7 and 14. Corrosion products from the sample surface post-immersion were removed using a solution containing 20 g $CrO_3$ and 1.9 g $AgNO_3$ dissolved in 100 mL of de-ionized water. The corroded samples were analyzed using SEM and Energy Dispersive X-Ray Spectroscopy (EDS) to gain more insight into the corrosion mechanism observed in the samples. The corrosion rate was calculated using the Equation (1).

$$\text{Corrosion Rate } (CR) = \frac{K \times (W_i - W_f)}{\rho AT} \qquad (1)$$

where K, $W_i$ (g), $W_f$ (g), $\rho$ (g/cc), A ($cm^2$), T (h) are time conversion coefficient, the initial weight of the sample, final weight of the sample, density of the sample and immersion time, respectively.

Analysis of Microhardness of Magnesium Alloys

According to the Standard Test Method for Microindentation Hardness of Materials (ASTM E384-08), microhardness were measured on the extruded samples at an indention load of 245 mN for a holding time of 15 seconds. Shimadzu HMV automatic digital microhardness tester (Kyoto, Japan) with a Vickers indenter (square-based pyramidal-shaped diamond indenter with a phase angle of) 136° was used for the measurements.

Tables 2 and 3 show the grain size and microhardness results of the magnesium alloys.

TABLE 2

Grain size and phase analysis of the magnesium alloys

| Composition | Grain Size (μm) | Phases Present |
| --- | --- | --- |
| Mg—Zn—xSr | 8.58 ± 1.65 | $Mg_{17}Sr_2$ |
| Mg—Zn—xDy—ySr | 6.397 ± 1.498 | $Mg_{17}Sr_2$ |
| Mg—Zn—xDy—xSr | 5.736 ± 0.955 | $Mg_{17}Sr_2$ |
| Mg—Zn—xDy—zSr | 4.044 ± 0.729 | $Mg_{17}Sr_2$ |

TABLE 3

Microhardness of the magnesium alloys

| Composition | Microhardness (Hv) |
| --- | --- |
| Mg—Zn—xSr | 108 ± 6 |
| Mg—Zn—xDy—ySr | 108 ± 5 |
| Mg—Zn—xDy—xSr | 105 ± 4 |
| Mg—Zn—xDy—zSr | 113 ± 4 |
| Mg—Zn—aCa—bMn | 166 ± 12 |
| Mg—Zn—aCa—cMn | 170 ± 10 |
| Mg—Zn—aCa—dMn | 164 ± 9 |

As shown in Table 2, the average grain size decreases with the presence of Dy and with the increased addition of Sr and is at the smallest for Mg—Zn-xDy-zSr. The microhardness for Mg—Zn-xDy-zSr is the highest.

FIG. 1 shows the grain size morphology of the magnesium alloys studied under the optical microscope. As shown in FIG. 1, a near equiaxed grain morphology of the magnesium alloys, more predominantly Mg—Zn-xDy-zSr, indicates an improvement in strength, corrosion and biocompatibility response. Therefore, the inventors have found that the high microhardness in the magnesium alloys can be attributed to (a) solid solution strengthening of Zn in Mg melt, (b) resistance offered to localized plastic deformation by secondary phase particles in the matrix and (c) refinement in grain size, as illustrated in FIG. 1.

Further, FIG. 2 shows the optical micrograph analysis of the magnesium alloys. A near-uniform secondary phase distribution is observed and it further confirmed the importance of the selection of processing parameters during the processing steps. The formation of a near uniform secondary phase, $Mg_{17}Sr_2$, is evident in FIG. 2.

Example 3: Determination of Corrosion Rate of Magnesium Alloys

In order to target magnesium-based alloys and composites as a bioresorbable implant, high corrosion resistance is crucial to retain the load-bearing strength with minimum inflammatory behavior. The corrosion rates of magnesium alloys was investigated using Hank's balanced salt solution (HBSS). The HBSS was regularly changed to keep the pH equivalent to the body fluid. The corrosion rate measurements are tabulated in Table 3. FIG. 3 shows the graph of corrosion rate against time of immersion (days) of the magnesium alloys.

TABLE 4

| Corrosion rate of magnesium alloys | | | | |
| --- | --- | --- | --- | --- |
| Time of Immersion | Corrosion Rate (mm/y) of Magnesium Alloys | | | |
| (days) | Mg—Zn—xSr | Mg—Zn—xDy—ySr | Mg—Zn—xDy—xSr | Mg—Zn—xDy—zSr |
| 1 | 0.201 | 0.2061 | 0.1846 | 0.3693 |
| 2 | 0.1989 | 0.1979 | 0.1683 | 0.2489 |
| 3 | 0.1938 | 0.1622 | 0.1295 | 0.2346 |
| 4 | 0.11857 | 0.1581 | 0.1836 | 0.2163 |
| 7 | 0.1775 | 0.1326 | 0.1428 | 0.1693 |
| 14 | 0.154 | 0.1183 | 0.1469 | 0.1408 |

Both Table 4 and FIG. 3 shows the corrosion rate of the magnesium alloys. The corrosion rate of the alloys was observed to be high for all samples at the end of day 1, minor fluctuations till the end of day 4 and a near-uniform or declining rate thereafter till the end of the cycle at 14 days, with less than 0.2 mm/y remaining. This is further explained by the anodic dissolution of Mg into $Mg^{2+}$ which results in the increased corrosion rate from day 0 to day 1. A protective magnesium hydroxide layer is formed due to the ionic interaction between $Mg^{2+}$ and $OH^-$. This results in a decrease in the corrosion rate as the hydroxide layer forms a diffusion barrier between the matrix and the solution. The low radius Cl-ions diffuse through the layer and interacts with the surface resulting in localized pits and with the secondary phases causing micro galvanic corrosion.

Example 4: Cell Viability Testing of Magnesium Alloys

Biosafety of an implant materials can be assessed by biocompatibility testing. The cell viability testing is the most important and commonly used cytocompatibility test.

Osteoblast-like murine MC3T3-E1 cells were used for the cell culture. Alpha-Minimum Essential Medium (MEM) (Gibco) supplemented with 10% Fetal Bovine Serum and 1% Penicillin-Streptomycin were used as culture medium. Cells were incubated in a humidified atmosphere at 37° C. and at 5% $CO_2$. For the direct assay, 5 mm×2 mm discs were used. Cells were directly seeded on the discs. The direct Assay® was performed in 96-well-plates. MTS solution (CellTiter 96 Aqueous Assay System from Promega) was used for the cell proliferation assay. MC3T3-E1 (8000 cells) were seeded directly on the discs in 96 well plate and incubated for 1, 3 and 5 days. After the incubation period, the samples with the cells were washed with Phosphate Buffered Saline (PBS) and 100 µl of alpha MEM media was added to the wells. 20 µl of MTS reagent was added to the wells under a dark environment and incubated for 2 hours at 37° C. in 5% $CO_2$. After the incubation, the well plate was read for optical density values in 96 well plate reader at 490 nm wavelength. Optical Density (OD) values obtained from the well plate reader were plotted and the percentage of viable cells was calculated using Equation (2).

$$\text{Percentage of viable cell } (\%) = \frac{\text{Experimental } (OD) \text{ values}}{\text{Control } (OD) \text{ values}} \times 100 \quad (2)$$

TABLE 5

| Cell viability testing of magnesium alloys | | | |
| --- | --- | --- | --- |
| Type of Magnesium Alloys | Cell Survival (% of Control) at Time Period of Day 1, 3 and 5 | | |
| | Day 1 | Day 3 | Day 5 |
| Mg—Zn—xSr | 98.515 | 110.514 | 91.289 |
| Mg—Zn—xDy—xSr | 106.412 | 125.144 | 112.043 |
| Mg—Zn—xDy—zSr | 90.431 | 94.462 | 77.074 |
| Mg—Zn—aCa—bMn | 112.68 | 139.17 | 125.98 |
| Mg—Zn—aCa—cMn | 104.87 | 121.64 | 109.86 |
| Mg—Zn—aCa—dMn | 101.68 | 115.71 | 108.06 |

FIGS. 6A and 6B show the cell viability of MC3T3-E1 pre-osteoblast cells expressed as a percentage of the viability of cells cultured in the negative control after incubation for 1, 3, and 5 days of the magnesium alloys. Referring to both Table 5 and FIGS. 6A and 6B, the cell viability of all the alloys increased at the end of day 3, displaying a significant improvement. Further, the cell viability values of the materials decreased with the passage of time although exhibiting no signs of cytotoxicity to MC3T3-E1 cells. As per the ISO 10993-5:2009 standard for MTT assay, if the cell viability percentage is greater than 70% of the negative control, the alloys have zero cytotoxicity potential. The improved cytotoxicity results are be attributed to (a) refined grain structure, (b) high surface energy, (c) corrosion control and (d) biologically active apatite layer formation.

Comparative Example

Comparative Example 1: Testing of Compression Properties

To investigate the compressive properties of the magnesium alloys, quasi-static compression tests were conducted as stated in the Standard Test Method of Compression Testing of Metallic Materials at Room Temperature (ASTM E9-89a). At room temperature, cylindrical samples with internal diameter ($\Phi$) 8 mm×8 mm were tested using 810 Material Testing Systems (MTS) at a strain rate of $8.3 \times 10^{-5}$ per second. A minimum of five samples was tested to ensure consistent and reproducible results. Table 6 shows the compression testing results of the magnesium alloys with commercially used magnesium alloys.

TABLE 6

Compression testing results of the magnesium alloys with commercially used magnesium alloys and metallic biomaterials

| Material | 0.2CYS (Compressive Yield Strength, MPa) | UCS (Ultimate Compressive Strength, MPa) | Fracture strain (%) |
|---|---|---|---|
| Mg—Zn—xSr | 103.7 ± 6.5 | 410.2 ± 21.1 | 18.2 ± 0.9 |
| Mg—Zn—xDy—ySr | 143.49 ± 4.02 | 449.39 ± 9.80 | 20.93 ± 0.78 |
| Mg—Zn—xDy—xSr | 157.90 ± 15.26 | 466.37 ± 8.09 | 15.13 ± 4.21 |
| Mg—Zn—xDy—zSr | 204 ± 22 | 494.08 ± 68.78 | 18.60 ± 2.94 |
| Mg—Zn—aCa—bMn | 226 ± 6.5 | 630 ± 11.7 | 14.08 ± 0.2 |
| Mg—Zn—aCa—cMn | 251 ± 4.1 | 645 ± 7.5 | 13.97 ± 0.6 |
| Mg—Zn—aCa—dMn | 249 ± 2.2 | 617 ± 12 | 13.53 ± 0.9 |
| Mg—5Zn/5BG (Mg-5 wt % Zn-5 wt % bioglass) | — | 112.8 | — |
| Mg—3Zn-(2,5,10)HA (Mg-3 wt % Zn - (2, 5, 10) wt % hydroxyapatite) | 80-98 | 116-134 | 14-17 |
| Mg—6.5Zn-(5, 10, 15, 20)HA (Mg-6.5 wt % Zn - (5, 10, 15, 20) wt % hydroxyapatite) | — | 249-292 | 0.52-1.36 |
| Mg—6Zn/10β-TCP (Mg-6 wt % Zn-10 wt % β- tricalcium phosphate) | 162 | 332 | — |
| AZ31 (Mg-3 wt % Al-1 wt % Zn (impurities like Mn, Si, Cu, Fe, Ni combine < 0.4 wt %)) | — | 250 | 28 |
| AZ91D (Mg-9 wt % Al-1 wt % Zn (impurities like Mn, Si, Cu, Fe, Ni combine < 0.4 wt %)) | 130 | 300 | 12.4 |
| AM50 (Mg-5 wt % Al-0.4 wt % Mn-0.2 wt % Zn (impurities like Si, Cu, Fe, Ni combine < 0.4 wt %)) | 110 | 312 | 11.5 |
| WE43 (Mg-4 wt % Y-3 wt % Nd-0.7 wt % Zr (impurities like Li, Si, Cu, Fe, Ni, Mn combine < 0.4 wt %)) | 261 ± 16 | 420 ± 13 | 16.3 ± 1.0 |
| ZK60 (Mg-5 wt % Zn-0.45 wt % Zr) | 159 | 472 | 12.4 |
| WE54 (Mg-5 wt % Y-1.75 wt % Nd-0.7 wt % Zr (impurities like Li, Si, Cu, Fe, Ni, Mn combine < 0.4 wt %)) | 210 | 325 | 27 |
| Stainless steel (<0.03% C, 16-18.5% Cr, 10-14% Ni, 2-3% Mo, <2% Mn, <1% Si, <0.045% P, <0.03% S, balance Fe) | — | 170-310 | — |

TABLE 6-continued

Compression testing results of the magnesium alloys with commercially used magnesium alloys and metallic biomaterials

| Material | 0.2CYS (Compressive Yield Strength, MPa) | UCS (Ultimate Compressive Strength, MPa) | Fracture strain (%) |
|---|---|---|---|
| Titanium alloy (5.5-6.76% Al, 3.5-4.5% V, C < 0.08%, Fe < 0.25%, balance T) | — | 758-1117 | 29-49 |
| Natural bone | 130-180 | — | — |
| Cortical bone | — | 131-224 | 2-12 |
| Femur | — | 167 | — |
| Tibia | — | 159 | — |

As shown in Table 6, the room temperature compressive yield strength (CYS) and were found to increase with the presence of increase in weight % of Dy, Sr, Ca and Mn. The results of the compression testing were compared with other commercially-used magnesium alloys and also natural bone samples. The compression testing results of the magnesium alloys is even better than commercially-used magnesium alloys such as Mg-6Zn/10β-TCP, AZ91D, AM50, WE43+ Apatite, and ZK60.

INDUSTRIAL APPLICABILITY

The disclosed magnesium alloys contain suitable alloying elements like zinc and biocompatible elements such as dysprosium, strontium, calcium and manganese. The alloys do not contain aluminum, which is neurotoxic, or rare elements like yttrium, which is cytotoxic. Advantageously, the magnesium-based alloys possess properties such as chemical inertness, high strength, rigidity, stability, biocompatibility, tissue receptivity and resistance to corrosion, making it an ideal and safe material for orthopedic applications and implants.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:
1. A method for producing an alloy of Formula (I):

Mg—Zn—X        Formula (I)

wherein:
  X represents —Ca—Mn or —Dy—Sr;
Mg is magnesium, Zn is zinc, Dy is dysprosium, Sr is strontium, Ca is calcium and Mn is manganese;
wherein said alloy comprises, based on total weight:
about 0.1 wt % to about 3.0 wt % Zn,
about 0.1 wt % to about 0.7 wt % Dy,
about 0.1 wt % to about 0.9 wt % Sr, and
balance of Mg and impurities; or
about 0.1 wt % to about 3.0 wt % Zn,
about 0.1 wt % to about 1.5 wt % Ca,
about 0.1 wt % to about 0.9 wt % Mn, and
balance of Mg and impurities;
wherein said method comprises:
  (a) placing alloy components in a crucible, wherein the alloy components are placed in the crucible in a multilayer arrangement;

(b) melting the alloy components at about 700° C. to about 850° C. to form a first melt;

(c) stirring the first melt of step (b) at about 400 rpm to about 500 rpm to form a second melt;

(d) atomizing the second melt of step (c) into millimeter size droplets using jets of inert gas;

(e) cooling and depositing the millimeter size droplets of step (d) to obtain an ingot;

wherein the multilayer arrangement of step (a) comprises an A-B-A arrangement, wherein A consists of a first alloy component and B consists of a second alloy component, wherein the first and second alloy components each consist of a single alloy material or a blended alloy mixture of two or more alloy materials; or wherein the multilayer arrangement of step (a) comprises an A-B-A-B-A arrangement, wherein A consists of a first alloy component and B consists of a second alloy component, wherein the first and second alloy components each consist of a single alloy material or a blended alloy mixture of two or more alloy materials.

2. The method of claim 1, wherein step (a) comprises controlling the volume of the alloy components to 70% to 75% the volume of the crucible.

3. The method of claim 1, wherein A consists of magnesium and B consists of a blended alloy mixture of zinc and X.

4. The method of claim 1, wherein each layer of the multilayer arrangement is of equal volume.

5. The method of claim 1, wherein step (d) comprises using 2 to 4 jets of inert gas.

6. The method of claim 1, wherein the inert gas in step (d) is argon.

7. The method of claim 1, wherein each jet in step (d) has a diameter of about 1 mm to about 2 mm.

8. The method of claim 1, wherein each jet in step (d) has a gas flow rate of about 20 to about 30 litres per minute.

9. The method of claim 1, further comprising step (f) subjecting the ingot to hot extrusion at about 250° C. to about 400° C.

10. The method of claim 9, wherein the hot extrusion has an extrusion ratio range of from 25:1 to 12:1.

11. The method of claim 1, wherein the alloy comprises, based on total weight:

about 0.8 wt % to about 1.6 wt % Zn, about 0.3 wt % to about 0.9 wt % Ca, about 0.1 wt % to about 0.5 wt % Mn, and balance of Mg and impurities.

\* \* \* \* \*